US012031973B1

(12) United States Patent
Sjöland et al.

(10) Patent No.: US 12,031,973 B1
(45) Date of Patent: Jul. 9, 2024

(54) SYSTEM METHOD FOR DETERMINATION OF HUMIDITY OF CONCRETE

(71) Applicant: Zenzr Sverige AB, Lund (SE)

(72) Inventors: Johan Sjöland, Bunkeflostrand (SE); Anders Hörberg, Lund (SE)

(73) Assignee: Zenzr Sverige AB, Lund (SE)

( * ) Notice: Subject to any disclaimer, the term of this patent is extended or adjusted under 35 U.S.C. 154(b) by 0 days.

(21) Appl. No.: 18/563,949

(22) PCT Filed: May 25, 2022

(86) PCT No.: PCT/SE2022/050510
§ 371 (c)(1),
(2) Date: Nov. 24, 2023

(87) PCT Pub. No.: WO2022/250601
PCT Pub. Date: Dec. 1, 2022

(30) Foreign Application Priority Data

May 28, 2021 (SE) .................................. 2150686-0

(51) Int. Cl.
*G01N 33/38* (2006.01)
*G08C 17/02* (2006.01)
(52) U.S. Cl.
CPC ........... *G01N 33/383* (2013.01); *G08C 17/02* (2013.01)
(58) Field of Classification Search
CPC .............................. G08C 17/02; G01N 33/383
See application file for complete search history.

(56) References Cited

U.S. PATENT DOCUMENTS

| 10,352,894 B2 | 7/2019 | Akasaka |
| 10,768,130 B2 | 9/2020 | Ghods |
| 2016/0266086 A1* | 9/2016 | Von Herzen ....... G01N 29/2481 |
| 2017/0160111 A1* | 6/2017 | Dowdall ............. G01N 33/383 |

(Continued)

FOREIGN PATENT DOCUMENTS

| KR | 101667137 B1 | 10/2016 |
| WO | 2020210861 A1 | 10/2020 |

OTHER PUBLICATIONS

International Search Report from corresponding International Application No. PCT/SE2022/050510, mailed on Aug. 23, 2022, 4 pages.

(Continued)

*Primary Examiner* — Nathaniel J Kolb
(74) *Attorney, Agent, or Firm* — Tucker Ellis LLP

(57) ABSTRACT

The disclosure relates to a system (100) for determination of humidity of concrete, the system (100) comprises a gauge (A1,A2,A3) configured to be embedded into the concrete, a first wireless communication module (10a, 10b, 10c) configured for wide area radio communication, and a processing circuitry (102a, 102b, 102c) operatively connected to the a gauge (A1,A2,A3) and the wireless communication module (10a, 10b, 10c), configured to cause the system (100) to obtain first measurement data by the gauge (A1,A2,A3), and transfer data wirelessly by the wireless communication module (10a, 10b, 10c) for making a value, defining the humidity of the concrete, available at a remote location. The disclosure further relates to a method for determination of humidity of concrete and a computer program product (500).

9 Claims, 5 Drawing Sheets

(56) References Cited

U.S. PATENT DOCUMENTS

2017/0284996 A1* 10/2017 Ghods .................. G01N 33/383
2018/0052146 A1* 2/2018 Radjy .................. G01N 33/383

OTHER PUBLICATIONS

M.J. Correia et al., "Sensor for oxygen evaluation in concrete," Cement and Concrete Composites, vol. 28, Issue 3; acquired from Internet at: https://www.sciencedirect.com/science/article/abs/pii/S095894650600014X#preview-section-snippets, Mar. 2006, pp. 226-232.

International Preliminary Report on Patentability from corresponding International Application No. PCT/SE2022/050510, mailed on Apr. 17, 2023, 16 pages.

\* cited by examiner

SYSTEM METHOD FOR DETERMINATION OF HUMIDITY OF CONCRETE

TECHNICAL FIELD

The present disclosure relates to a system for determination of humidity of concrete, a method for determination of humidity of concrete and a computer program product. More specifically, the disclosure relates to a system for determination of humidity of concrete, a method for determination of humidity of concrete and a computer program product.

BACKGROUND ART

Many constructions today are built using concrete. Concrete can for example consist of sand, gravel or crushed rock mixed with water and cement. The cement is often a finely ground powder with a bonding function. Example of constructions built of concrete are buildings, bridges, roads, tunnels, harbors, etc. Asphalt is also a concrete usually used for road constructions.

Often when using concrete, one need to know the humidity of the concrete in order to understand the quality of the concrete. This is crucial in order to e.g. proceed with further building of the construction.

Measurements of the humidity of concrete is today often achieved by drilling plural holes into a concrete surface of a concrete object, e.g. part of a construction, in order to place a humidity sensor into the hole. The hole is then often covered and the humidity sensor rests in the hole of the concrete object. It often requires plural days to establish a humidity equilibrium in the cavity create by the hole in order to do correct measurements of the humidity of the concrete by the humidity sensor. The measurements of the humidity is often made by a user that is at the construction in the vicinity of the humidity sensor.

Humidity sensors are often saturated or short-circuited, when the humidity is above 80% which causes false measurements.

Difficulties in obtaining the humidity of the concrete can e.g. cause delay in the construction or cause an uncertainty in determining the quality of the concrete, which can have an impact on the robustness of a concrete construction, but and also make a the concrete construction more expensive and cause a delay in finishing the construction on time.

SUMMARY

There is a desire to measure the humidity in a way so that the use of a humidity sensor can be avoided to eliminate the problem with humidity sensors being saturated or short-circuited, when the humidity is above 80% which causes false measurements which is not desired.

There is also a desire to minimize the time to determine the humidity of the concrete and to eliminate the waiting time of waiting plural days as required to establish a humidity equilibrium as required to do the measurements of the humidity of the concrete by a humidity sensor.

There is also a desire is to avoid drilling holes into the concrete, which is not only time consuming but also costly.

Yet a desire is to avoid the need of having users in the vicinity of the concrete for determining the humidity, but instead make a value, defining the humidity of the concrete, available at a remote location.

It is an object of the present disclosure to mitigate, alleviate or eliminate one or more of the above-identified deficiencies and disadvantages in the prior art and solve at least the above mentioned problem.

According to a first aspect there is provided a system for determination of humidity of concrete. The system comprises a gauge configured to be embedded into the concrete, a first wireless communication module configured for wide area radio communication and a processing circuitry operatively connected to the a gauge and the wireless communication module. The processing circuitry is configured to cause the system to obtain first measurement data by the gauge and transfer data wirelessly by the wireless communication module for making a value, defining the humidity of the concrete, available at a remote location.

One advantage with this first aspect is that there is no need for a user to be in the vicinity of the concrete, instead the humidity of the concrete can be made available at a remote location and the transfer of data can occur on a continuous basis or when needed. There is further no need to drill a hole and wait for a humidity equilibrium since the gauge is configured to be embedded into the concrete from the beginning when the object made of concrete is built.

According to some embodiments, the gauge comprises a gas sensor.

One advantage with this embodiment is that the gas at the gauge can be analyzed and the use of a humidity sensor can be avoided.

According to some embodiments, the gas sensor is an oxygen gas displacement sensor and the processing circuitry is further configured to determine the relative oxygen saturation at the gauge.

One advantage with this embodiment is that the gas at the gauge can be analyzed and a relative measure of the concentration of oxygen that is dissolved or carried in the concrete, as a proportion of the maximal concentration that can be dissolved in the concrete, can be determined.

According to some embodiments, the gauge further comprises an ammonia absorption system.

One advantage with this embodiment is that ammonia can be absorbed from the gas at the gauge for enhancing the accuracy of the gauge when obtaining measurement data.

According to some embodiments, the processing circuitry is further configured to determine the humidity at the gauge based on the determined relative oxygen saturation at the gauge.

One advantage with this embodiment is that the use of a humidity sensor can be eliminated and a determination of the humidity of the concrete at the gauge can instead be determined based on the determined relative oxygen saturation at the gauge.

According to some embodiments, the system further comprises a reference gauge configured to be placed in the environment surrounding the concrete with the embedded gauge, a second wireless communication module configured for wide area radio communication, and the processing circuitry is operatively connected to the reference gauge and configured to obtain second measurement data by the reference gauge.

One advantage with this embodiment is that obtained second measurement data of the environment surrounding the concrete with the embedded gauge can be used as reference data for determination of the humidity of the concrete at the gauge embedded in the concrete.

According to some embodiments, the gauge and/or the reference gauge further comprises a temperature sensor.

One advantage with this embodiment is that the temperature at the gauge and/or the reference gauge can be determined and used as reference data for the determination of the humidity of the concrete at the gauge embedded in the concrete.

According to some embodiments, the processing circuitry is further configured to determine the humidity at the gauge based on the first measurement data obtained by the gauge and based on the second measurement data obtained by the reference gauge.

One advantage with this embodiment is that obtained first measurement data obtained by the gauge embedded in the concrete and obtained second measurement data of the environment surrounding the concrete with the embedded gauge, can be used for determination of the humidity of the concrete at the gauge embedded in the concrete.

According to some embodiments, the processing circuitry is further configured to determine the humidity at the gauge based on the first measurement data obtained by the gauge and based on the second measurement data obtained by the reference gauge combined with chemical composition data of the concrete.

One advantage with this embodiment is that obtained first measurement data obtained by the gauge embedded in the concrete and obtained second measurement data of the environment surrounding the concrete with the embedded gauge combined with chemical composition data of the concrete, can be used for determination of the humidity of the concrete at the gauge embedded in the concrete that is determined with respect to the characteristics of the concrete.

According to a second aspect there is provided a method for determination of humidity of concrete, the method comprising the step of obtaining first measurement data by a gauge embedded into concrete, followed by the step of transferring data wirelessly by a wireless communication module for making a value, defining the humidity of the concrete, available at a remote location.

One advantage with this second aspect is that there is no need for a user to be in the vicinity of the concrete, instead the humidity of the concrete can be made available at a remote location and the transfer of data can occur on a continuous basis or when needed. There is further no need to drill a hole and wait for a humidity equilibrium since the gauge is configured to be embedded into the concrete from the beginning when the concrete object is built.

According to some embodiments, the method further comprises determining the relative oxygen saturation at the gauge.

One advantage with this embodiment is that the gas at the gauge can be analyzed and a relative measure of the concentration of oxygen that is dissolved or carried in the concrete, as a proportion of the maximal concentration that can be dissolved in the concrete, can be determined.

According to some embodiments, the method further comprises determining the humidity at the gauge based on the determined relative oxygen saturation at the gauge.

One advantage with this embodiment is that the use of a humidity sensor can be eliminated and a determination of the humidity of the concrete at the gauge can instead be determined based on the determined relative oxygen saturation at the gauge.

According to some embodiments, the method further comprises obtaining second measurement data by a reference gauge.

One advantage with this embodiment is that obtained second measurement data of the environment surrounding the concrete with the embedded gauge can be used as reference data for determination of the humidity of the concrete at the gauge embedded in the concrete.

According to some embodiments, the method further comprises determining the humidity at the gauge based on the first measurement data obtained by the gauge and based on the second measurement data obtained by the reference gauge.

One advantage with this embodiment is that obtained first measurement data obtained by the gauge embedded in the concrete and obtained second measurement data of the environment surrounding the concrete with the embedded gauge, can be used for determination of the humidity of the concrete at the gauge embedded in the concrete.

According to a third aspect there is provided a computer program product comprising a non-transitory computer readable medium, having thereon a computer program comprising program instructions, the computer program being loadable into a processing circuitry and configured to cause execution of the method when the computer program is run by the at least one processing circuitry.

Effects and features of the second and third aspects are to a large extent analogous to those described above in connection with the first aspect. Embodiments mentioned in relation to the first aspect are largely compatible with the second and third aspects.

The present disclosure will become apparent from the detailed description given below. The detailed description and specific examples disclose preferred embodiments of the disclosure by way of illustration only. Those skilled in the art understand from guidance in the detailed description that changes and modifications may be made within the scope of the disclosure.

Hence, it is to be understood that the herein disclosed disclosure is not limited to the particular component parts of the device described or steps of the methods described since such device and method may vary. It is also to be understood that the terminology used herein is for purpose of describing particular embodiments only, and is not intended to be limiting. It should be noted that, as used in the specification and the appended claim, the articles "a", "an", "the", and "said" are intended to mean that there are one or more of the elements unless the context explicitly dictates otherwise. Thus, for example, reference to "a unit" or "the unit" may include several devices, and the like. Furthermore, the words "comprising", "including", "containing" and similar wordings does not exclude other elements or steps.

BRIEF DESCRIPTIONS OF THE DRAWINGS

The above objects, as well as additional objects, features and advantages of the present disclosure, will be more fully appreciated by reference to the following illustrative and non-limiting detailed description of example embodiments of the present disclosure, when taken in conjunction with the accompanying drawings.

FIG. 1*a* illustrates an example system for determination of humidity of concrete according to an embodiment of the present disclosure.

FIG. 1*b* illustrates an example system for determination of humidity of concrete according to an embodiment of the present disclosure.

DETAILED DESCRIPTION

The present disclosure will now be described with reference to the accompanying drawings, in which preferred example embodiments of the disclosure are shown. The disclosure may, however, be embodied in other forms and should not be construed as limited to the herein disclosed embodiments. The disclosed embodiments are provided to fully convey the scope of the disclosure to the skilled person.

There is a desire to measure the humidity in a way so that the use of a humidity sensor can be avoided to eliminate the problem with humidity sensors being saturated or short-circuited, when the humidity is above 80% which causes false measurements which is not desired.

There is also a desire to minimize the time to determine the humidity of the concrete and to eliminate the waiting time of waiting plural days as required to establish a humidity equilibrium as required to do the measurements of the humidity of the concrete by a humidity sensor.

There is also a desire is to avoid drilling holes into the concrete, which is not only time consuming but also costly.

Yet a desire is to avoid the need of having users in the vicinity of the concrete for determining the humidity, but instead make a value, defining the humidity of the concrete, available at a remote location.

The inventors have come up with a solution according to the present disclosure to mitigate, alleviate or eliminate one or more of the above-identified deficiencies and disadvantages in the prior art and solve at least the above mentioned problem.

Figure 1A:
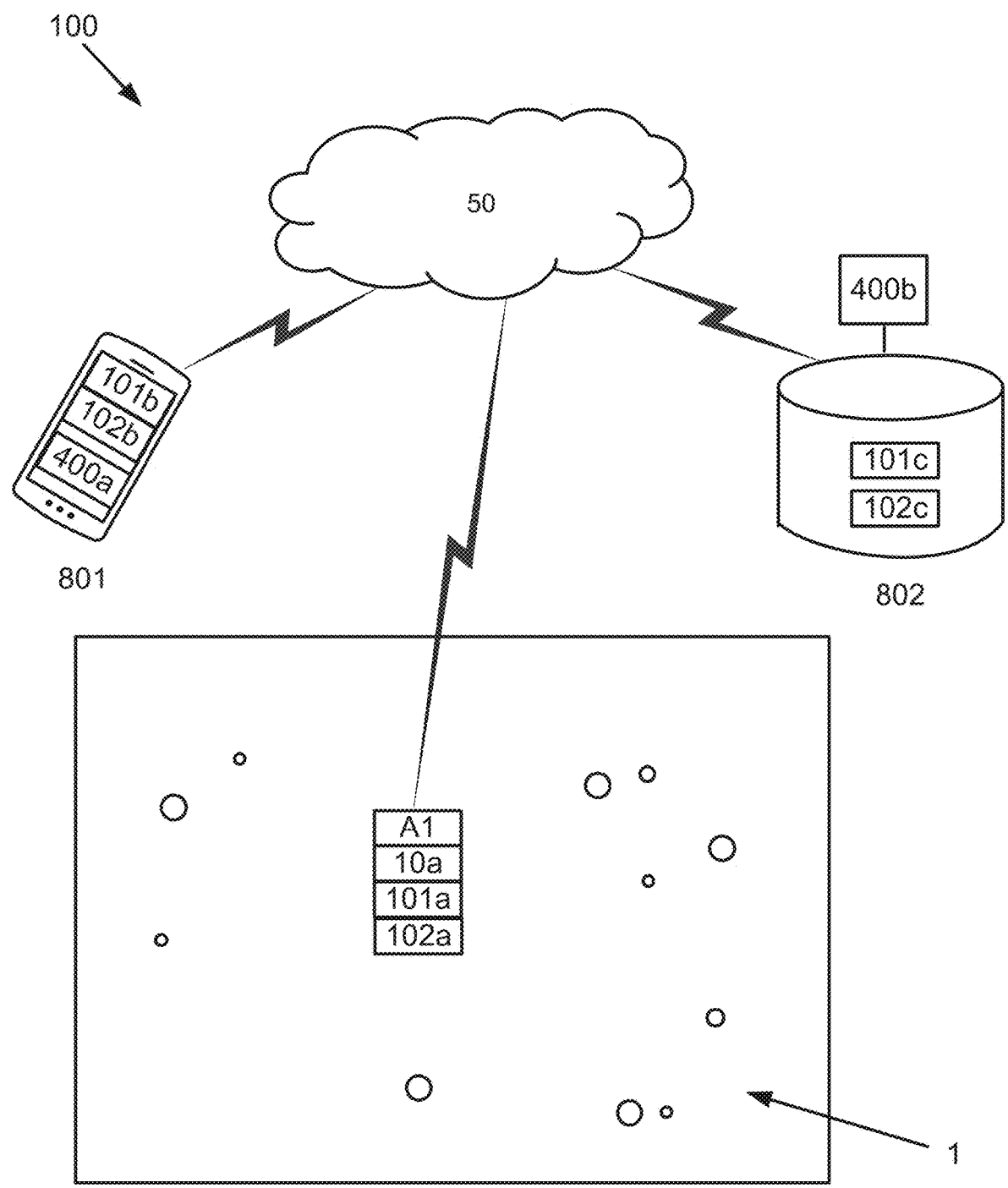

FIG. 1a illustrates an example system for determination of humidity of concrete according to an embodiment of the present disclosure. In particular, FIG. 1a illustrates an example system that comprises a gauge configured to be embedded into the concrete, for determination of humidity of concrete according to an embodiment of the present disclosure.

The first aspect of this disclosure shows a system 100 for determination of humidity of concrete.

Figure 1B:
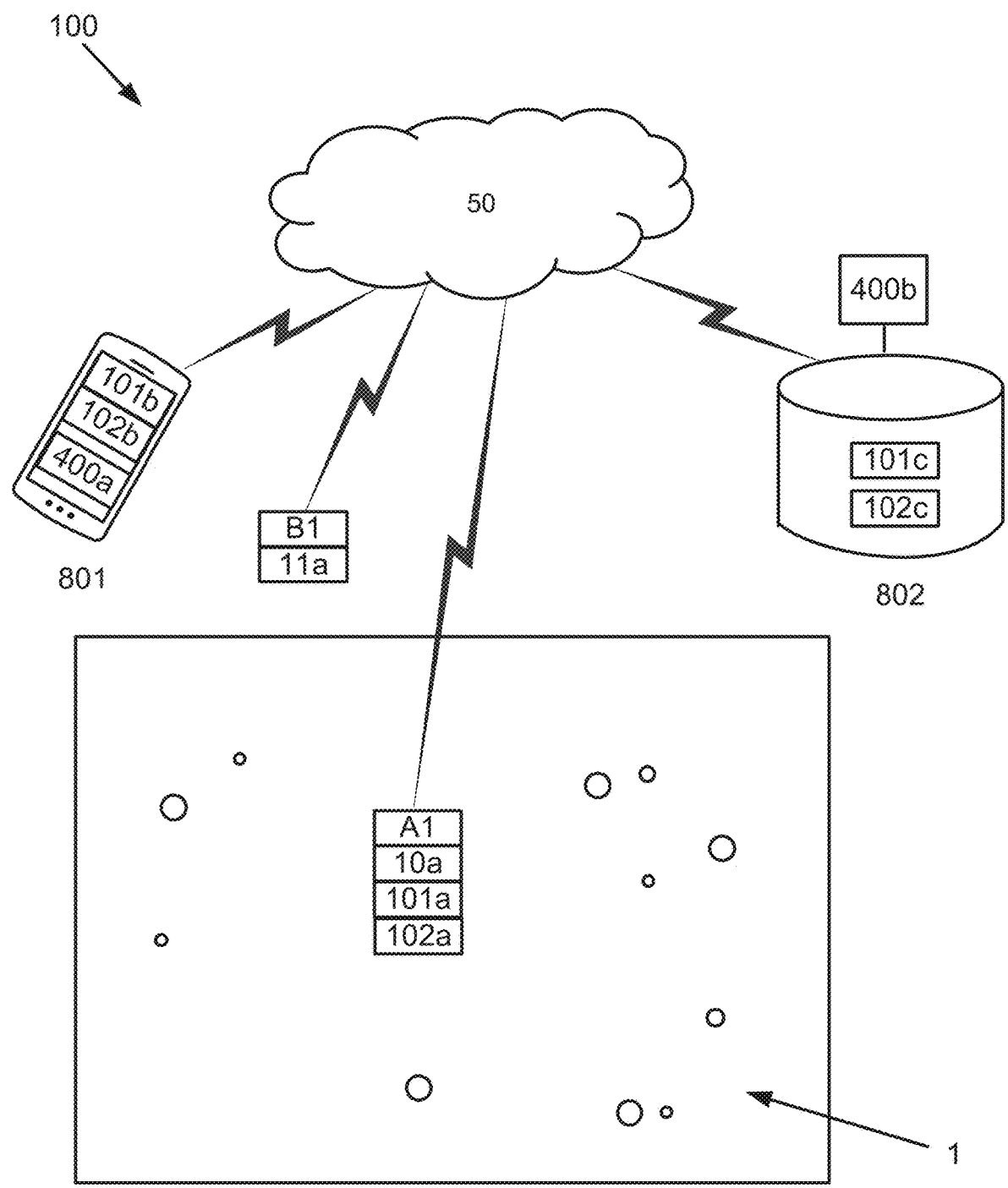
Figure 2:
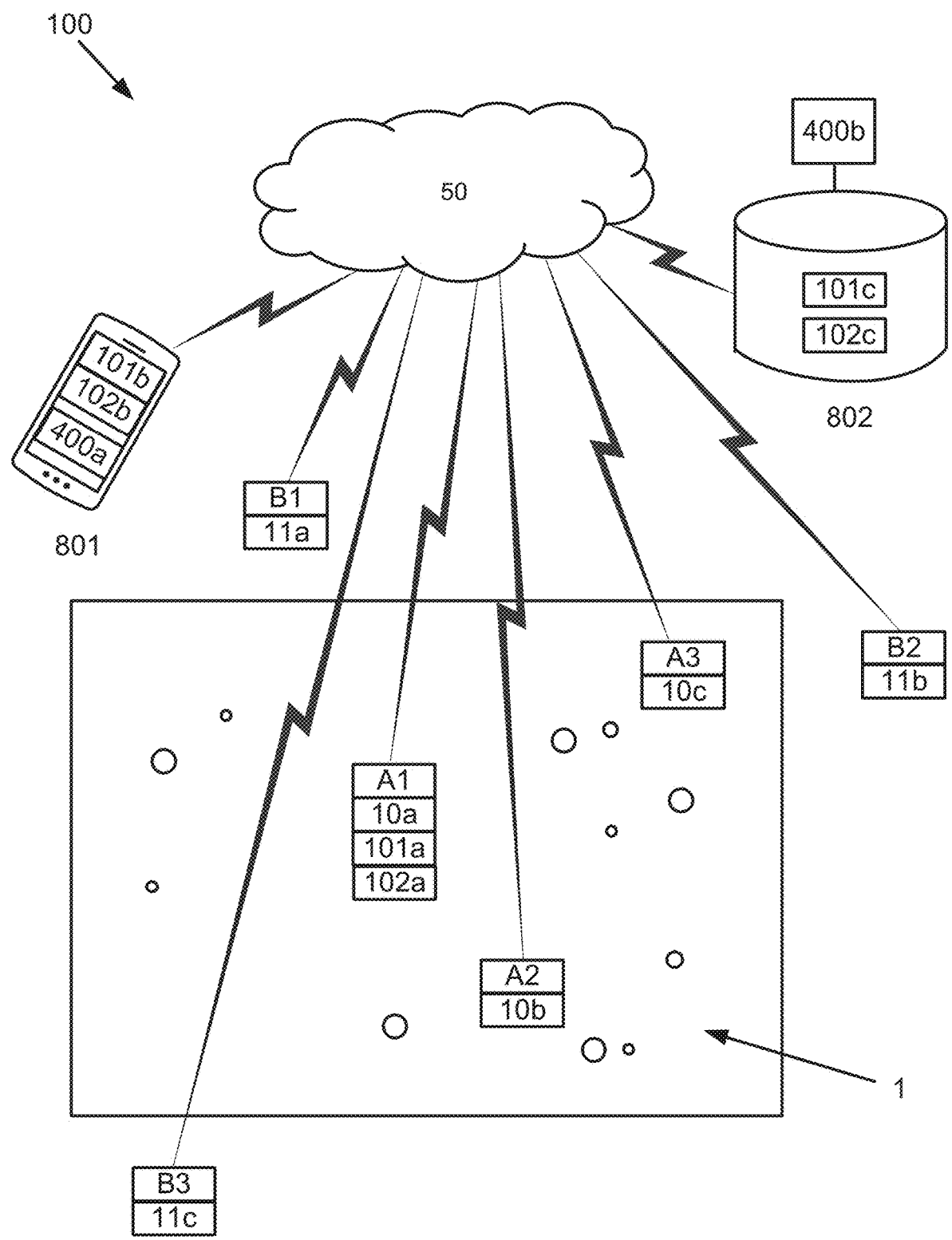
FIG. 2 illustrates an example system comprising plural gauges and plural reference gauges for determination of humidity of concrete according to an embodiment of the present disclosure.
Figure 3:
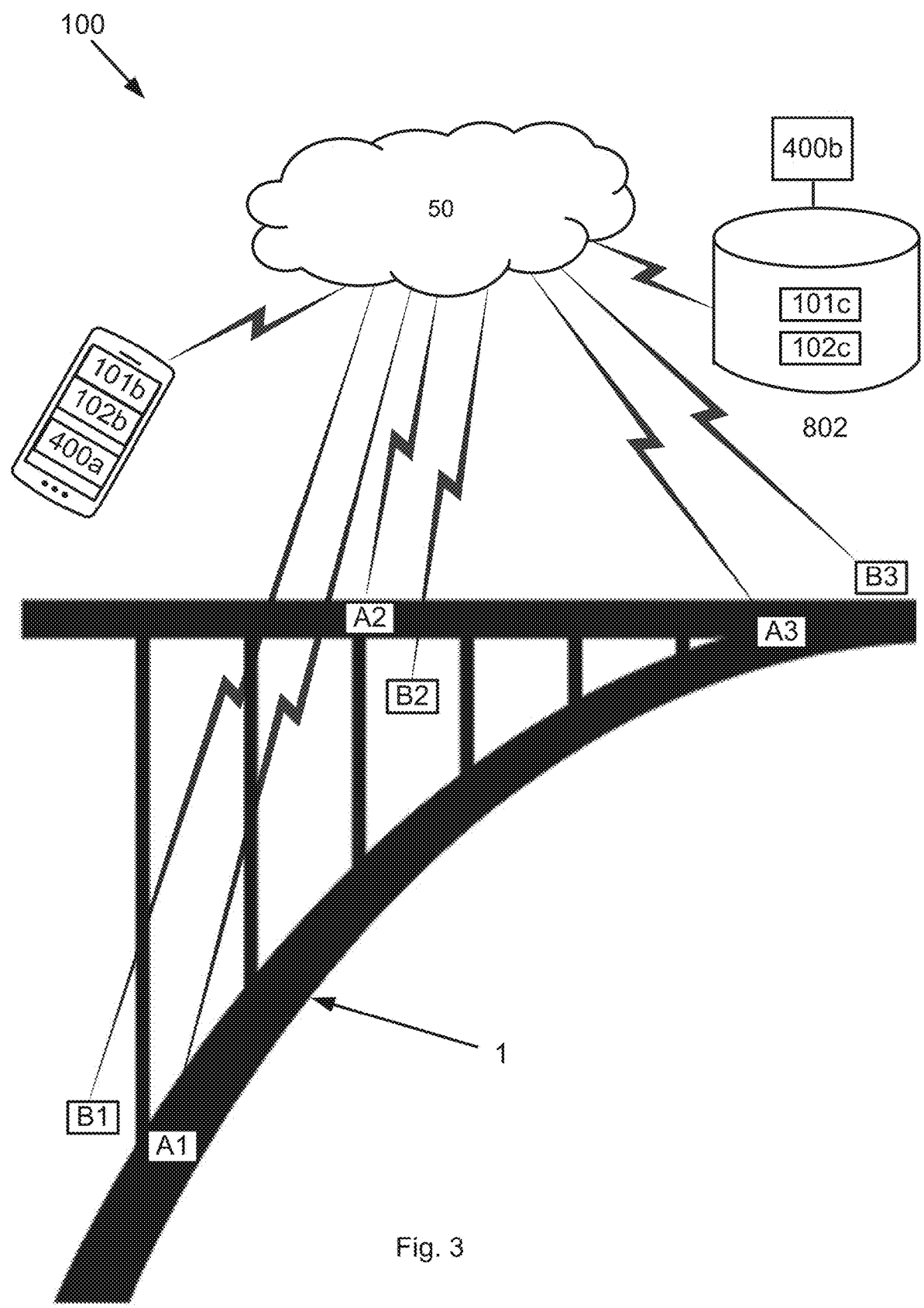
FIG. 3 illustrates an example system at a construction comprising plural gauges and plural reference gauges for determination of humidity of concrete according to an embodiment of the present disclosure.

The system 100 comprises a gauge A1,A2,A3 configured to be embedded into the concrete 1. FIG. 1a for example, illustrates an object that is made of concrete 1. Concrete can have a variety of forms and be part of e.g. of a construction such as a building, bridge, road, tunnel or harbor for example. In the illustration of FIGS. 1a, 1b and 2 the concrete is a rectangular block. In the example illustration of FIG. 3 concrete 1 is used in a bridge construction.

According to some embodiments the gauge A1,A2,A3 is arranged in a protective holder configured in order to be embedded into the concrete 1.

According to some embodiments the gauge A1,A2,A3 is a measurement instrument configured to obtain first measurement data. According to some embodiments the gauge A1,A2,A3 is configured to obtain first measurement data at gauge A1,A2,A3. According to some embodiments the first measurement data is obtained in a close proximity of the gauge A1,A2,A3.

The system 100 further comprises a first wireless communication module 10a, 10b,10c configured for wide area radio communication. According to some embodiments the first wireless communication module 10a,10b,10c is configured for wide area radio communication using a frequency between 430-923 MHZ, also known as long range, LoRa, communication.

An advantage with a frequency between 430-923 MHz, i.e. long range, LoRa communication, is that the radio signal penetrates concrete better than a local area radio communication interface such as a Wireless Local Area Network, WLAN, Bluetooth™, ZigBee, Ultra-Wideband, UWB, Radio Frequency Identification, RFID, or similar local area radio communication network. Hence, the first wireless communication module 10a,10b,10 is configured to communicate via wide area radio communication even if the first wireless communication module 10a,10b,10 is embedded into the concrete 1.

A further advantage with the long range, LoRa, communication, is that the radio signal propagates well over a wide area, so that there is no need to have users in the vicinity of the concrete 1 for determining the humidity, but instead a value, defining the humidity of the concrete, can be made available at a remote location via the long range, LoRa, communication. In an example long range, long range coverage, is well over 1000 meters.

According to some embodiments the first wireless communication module 10a,10b,10c is configured for communicating via a communication network 50, as illustrated in FIG. 1a.

According to some embodiments the communication network 50 is a wireless communication network.

According to some embodiments, the wireless communication network is a Long Range, LoRa, communication 430-923 MHz network. According to some embodiments, the wireless communication network is a standardized wireless wide area network such as a Global System for Mobile Communications, GSM, Extended GSM, General Packet Radio Service, GPRS, Enhanced Data Rates for GSM Evolution, EDGE, Wideband Code Division Multiple Access, WCDMA, Long Term Evolution, LTE, Narrowband-IoT, 5G, Worldwide Interoperability for Microwave Access, WiMAX or Ultra Mobile Broadband, UMB or similar network.

According to some embodiments the first wireless communication module 10a,10b,10c is further configured for local area radio communication. According to some embodiments the communication network 50 is a standardized wireless local area network such as a Wireless Local Area Network, WLAN, Bluetooth™, ZigBee, Ultra-Wideband, UWB, Radio Frequency Identification, RFID, or similar network.

According to some embodiments, the wireless communication network 50 can also be a combination of both a wireless local area network and a wireless wide area network. According to some embodiments, communication network 50 can be a combination a wired communication network and a wireless communication network.

According to some embodiments, the communication network 50 is defined by common Internet Protocols.

According to some embodiments the gauge A1,A2,A3 is arranged together with the first wireless communication module 10a,10b,10c and configured to be embedded into the concrete.

According to some embodiments the first wireless communication module 10a, 10b,10c and the gauge A1,A2,A3 are powered by a battery. According to some embodiments the first wireless communication module 10a,10b, 10c and the gauge A1,A2,A3 are powered by a battery configured to be charged via long range charging system.

According to some embodiments the system 100 comprises plural gauges A1, A2, A3 and each gauge A1, A2, A3 is operatively connected to a wireless communication module 10a, 10b, 10c. According to some embodiments the system 100 comprises plural gauges A1, A2, A3 and each gauge A1, A2, A3 is operatively connected to the same wireless communication module.

The system 100 further comprises a processing circuitry 102a,102b,102c operatively connected to the a gauge A1,A2,A3 and the wireless communication module 10a, 10b,10c.

According to some embodiments the processing circuitry 102a is a processing circuitry arranged at the gauge A1,A2, A3, as illustrated in FIG. 1a.

According to some embodiments the processing circuitry 102b is a processing circuitry of a portable electronic device 801, as illustrated in FIG. 1a. In an example the portable electronic device 801 is any of a smartphone or tablet connected to the gauge A1,A2,A3 via the communication network 50 as illustrated in FIG. 1a.

According to some embodiments the processing circuitry 102c is a processing circuitry of a remote server 802, as illustrated in FIG. 1a. In an example the remote server 802 is connected to the gauge A1,A2,A3 via the communication network 50 as illustrated in FIG. 1a.

According to some embodiments the system 100 comprises plural processing circuitries 102a, 102b,102c operatively connected to plural gauges A1,A2,A3 and plural wireless communication modules 10a,10b,10c as illustrated in FIG. 2.

According to some embodiments the processing circuitry 102a is arranged at the gauge A1 together with the wireless communication module 10a configured to be embedded into the concrete as illustrated in FIG. 1a.

According to some embodiments the gauge A1, A2, A3 is operatively connected to the wireless communication module 10a, 10b, 10c via a wired connection. According to some embodiments the gauge A1, A2, A3 is operatively connected to the wireless communication module 10a, 10b, 10c via a wireless communication interface configured for local area radio communication.

According to some embodiments the system 100 further comprises a memory 101a,101b,101c configured to store data, wherein the memory 101a,101b,101c is operatively connected to the processing circuitry 102a, 102b,102c.

According to some embodiments the memory 101a is a memory arranged at the gauge A1,A2,A3, as illustrated in FIG. 1a. According to some embodiments the memory 101b is a memory of a portable electronic device 801, as illustrated in FIG. 1a. According to some embodiments the memory 101c is a memory of a remote server 802, as illustrated in FIG. 1a.

According to some aspects the system 100 further comprises a user interface 400a, 400b, configured for input and output of data. According to some aspects the user interface 400a, 400b is configured for making a value, defining the humidity of the concrete, available for a user at a remote location from the concrete. In one example the user interface is a touch display of a portable electronic device 801 as illustrated in FIG. 1a. In one example the user interface is a display for output, and a keyboard for input, of a remote server 804 as illustrated in FIG. 1a.

The processing circuitry 102a, 102b, 102c is configured to cause the system 100 to obtain first measurement data by the gauge A1,A2,A3, and transfer data wirelessly by the wireless communication module 10a,10b, 10c for making a value, defining the humidity of the concrete, available at a remote location.

One advantage with this first aspect is that there is no need for a user to be in the vicinity of the concrete 1, instead the humidity of the concrete can be made available at a remote location and the transfer of data can occur on a continuous basis or when needed.

There is further no need to drill a hole and wait for a humidity equilibrium since the gauge A1,A2,A3 is configured to be embedded into the concrete 1 from the beginning when the object made of concrete is built.

According to some embodiments the system 100 is configured to continuously obtain first measurement data by the gauge A1,A2,A3, and continuously transfer data wirelessly by the wireless communication module 10a,10b, 10c for making a value, defining the humidity of the concrete, available at a remote location in real-time.

According to some embodiments the system 100 is configured to periodically obtain first measurement data by the gauge A1,A2,A3, and periodically transfer data wirelessly by the wireless communication module 10a, 10b, 10c for making a value, defining the humidity of the concrete, available at a remote location at predefined occasions.

According to some embodiments the first measurement data obtained by the gauge A1, A2, A3 is transferred wirelessly by the wireless communication module to a remote processing circuitry 102a, 102b, 102c for processing in order to make a value, defining the humidity of the concrete, available at a remote location.

According to some embodiments the first measurement data obtained by the gauge A1, A2, A3 is processed at a processing circuitry 102a arranged at the gauge A1, A2, A3, and the processed data is transferred wirelessly by the wireless communication module in order to make a value, defining the humidity of the concrete, available at a remote location.

According to some embodiments the processing circuitry 102a, 102b, 102c is configured to obtain input, via the user interface 400a, 400b, indicative of a request for making a value defining the humidity of the concrete available via the user interface 400a, 400b. In an example a user can on demand request a value defining the humidity of the concrete from a remote location.

According to some embodiments the gauge A1,A2,A3 comprises a gas sensor.

One advantage with this embodiment is that the gas at the gauge A1, A2, A3 can be analyzed and the use of a humidity sensor can be avoided.

According to some embodiments the gas sensor is an oxygen gas displacement sensor and the processing circuitry 102a,102b, 102c is further configured to determine the relative oxygen saturation % O at the gauge A1,A2,A3.

One advantage with this embodiment is that the gas at the gauge A1, A2, A3 can be analyzed and a relative measure of the concentration of oxygen that is dissolved or carried in the concrete 1, as a proportion of the maximal concentration that can be dissolved in the concrete, can be determined.

According to some embodiments the gauge A1, A2, A3 is an electrical conductivity meter. According to some embodiments the processing circuitry 102a,102b,102c is further configured to determine the electrical conductivity (S/m) at the gauge A1, A2, A3.

According to some embodiments the gauge A1,A2,A3 further comprises an ammonia absorption system.

One advantage with this embodiment is that ammonia can be absorbed from the gas at the gauge for enhancing the accuracy of the gauge when obtaining measurement data.

According to some embodiments the processing circuitry 102a,102b,102c is further configured to determine the humidity at the gauge A1,A2,A3 based on the determined relative oxygen saturation % O at the gauge A1,A2,A3.

One advantage with this embodiment is that the use of a humidity sensor can be eliminated and a determination of the humidity of the concrete at the gauge can instead be determined based on the determined relative oxygen saturation at the gauge.

According to some embodiments the first measurement data obtained by the gauge A1, A2, A3 comprising determined relative oxygen saturation % O at the gauge A1,A2,A3, is transferred wirelessly by the wireless communication module 10a, 10b, 10c to a remote processing circuitry 102b,102c for processing in order to make a value, defining the humidity of the concrete, available at a remote location.

According to some embodiments the first measurement data obtained by the gauge A1, A2, A3 comprising determined relative oxygen saturation % O at the gauge A1,A2, A3 is processed at a processing circuitry 102a arranged at the gauge A1, A2, A3, and the processed data is transferred wirelessly by the wireless communication module in order to make a value, defining the humidity of the concrete, available at a remote location.

According to some embodiments the processing circuitry 102a, 102b,102c is further configured to determine the humidity at the gauge A1,A2,A3 based on the determined relative oxygen saturation % O at the gauge A1,A2,A3 and based on the determined electrical conductivity (S/m) at the gauge A1, A2, A3.

According to some embodiments the system 100 further comprises a reference gauge B1, B2, B3 configured to be placed in the environment surrounding the concrete with the embedded gauge A1,A2,A3, a second wireless communication module 11a,11b,11c configured for wide area radio communication, and the processing circuitry 102a,102b, 102c is operatively connected to the reference gauge B1,B2, B3 and configured to obtain second measurement data by the reference gauge B1,B2,B3.

One advantage with this embodiment is that obtained second measurement data of the environment surrounding the concrete 1 with the embedded gauge A1,A2,A3 can be used as reference data for determination of the humidity of the concrete 1 at the gauge A1,A2,A3 embedded in the concrete.

FIG. 1b illustrates an example system 100 for determination of humidity of concrete according to an embodiment of the present disclosure. In particular, FIG. 1a illustrates an example system 100 that comprises a gauge A1,A2,A3 configured to be embedded into the concrete 1 and a reference gauge B1,B2,B3 configured to be placed in the environment surrounding the concrete with the embedded gauge A1,A2,A3, for determination of humidity of concrete according to an embodiment of the present disclosure.

According to some embodiments the reference gauge B1,B2, B3 is a measurement instrument configured to obtain second measurement data. According to some embodiments the reference gauge B1, B2, B3 is configured to obtain second measurement data at the reference gauge B1,B2,B3. According to some embodiments the first measurement data is obtained in a close proximity of the reference gauge B1,B2,B3.

According to some embodiments the second wireless communication module 11a,11b,11c is configured for wide area radio communication using a frequency between 430-923 MHz, also known as long range, LoRa, communication.

According to some embodiments the second wireless communication module 11a,11b,11c is configured for communicating via the communication network 50, as illustrated in FIG. 1b. According to some embodiments the second wireless communication module 11a,11b,11c is further configured for local area radio communication.

According to some embodiments the reference gauge B1,B2,B3 is arranged together with the second wireless communication module 11a,11b,11c and configured to be placed in the environment surrounding the concrete with the embedded gauge A1,A2,A3.

According to some embodiments the gauge A1,A2,A3 and/or the reference gauge B1,B2,B3 further comprises a temperature sensor.

According to some embodiments the processing circuitry 102a,102b,102c is further configured to determine the humidity at the gauge A1,A2,A3 based on the determined relative oxygen saturation % O at the gauge A1,A2,A3 and based on the temperature at the A1,A2,A3 and/or the reference gauge B1,B2,B3.

One advantage with this embodiment is that the temperature at the gauge A1,A2,A3 and/or the reference gauge B1, B2,B3 can be determined and used as reference data for the determination of the humidity of the concrete at the gauge A1,A2,A3 embedded in the concrete 1.

According to some embodiments the processing circuitry 102a,102b,102c is further configured to determine the humidity at the gauge A1,A2,A3 based on the first measurement data obtained by the gauge A1,A2,A3 and based on the second measurement data obtained by the reference gauge B1,B2,B3.

One advantage with this embodiment is that obtained first measurement data obtained by the gauge A1,A2,A3 embedded in the concrete 1 and obtained second measurement data of the environment surrounding the concrete 1 with the embedded gauge A1,A2,A3, can be used for determination of the humidity of the concrete at the gauge A1,A2,A3 embedded in the concrete 1.

According to some embodiments historic reference data of previously obtained first measurement data obtained by the gauge A1,A2,A3 embedded in the concrete 1 and previously obtained second measurement data of the environment surrounding the concrete 1 with the embedded gauge A1,A2,A3, can be used for determination of the humidity of the concrete at the gauge A1,A2,A3 embedded in the concrete 1.

According to some embodiments historic reference data of previously obtained first measurement data obtained by the gauge A1,A2,A3 embedded in the concrete 1 and previously obtained second measurement data of the environment surrounding the concrete 1 with the embedded gauge A1,A2,A3 is stored in the memory 101a, 101b, 101c and obtained from the memory 101a, 101b, 101c for determination of the humidity of the concrete at the gauge A1,A2, A3 embedded in the concrete 1.

According to some embodiments the processing circuitry 102a, 102b,102c is further configured to determine the humidity at the gauge A1,A2,A3 based on the first measurement data obtained by the gauge A1,A2,A3 and based on the second measurement data obtained by the reference gauge B1,B2, B3 combined with chemical composition data of the concrete.

One advantage with this embodiment is that obtained first measurement data obtained by the gauge embedded in the concrete and obtained second measurement data of the environment surrounding the concrete with the embedded gauge combined with chemical composition data of the concrete, can be used for determination of the humidity of the concrete at the gauge embedded in the concrete that is determined with respect to the characteristics of the concrete.

According to some embodiments the user interface 400a, 400b is used for inputting chemical composition data of the concrete According to some embodiments the processing circuitry 102a, 102b, 102c is configured to obtain input, via the user interface 400a, 400b, indicative of chemical composition data of the concrete to be used to determine the humidity at the gauge A1,A2,A3.

Figure 4:
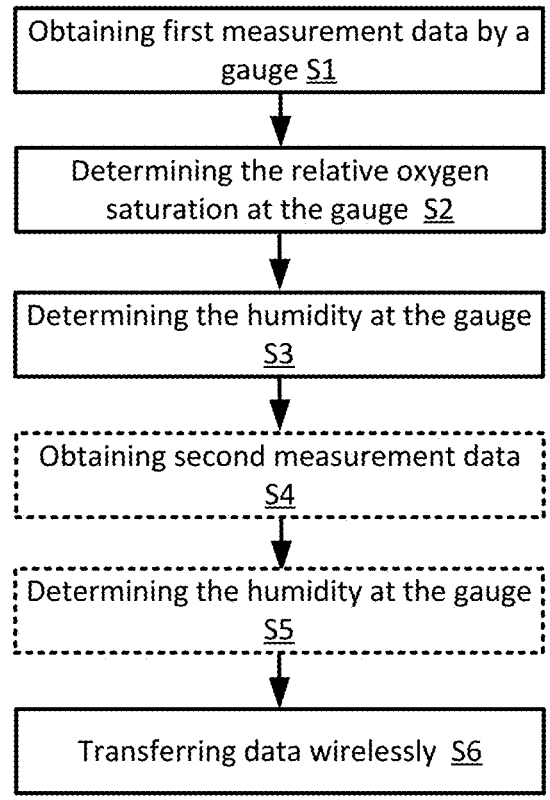
FIG. 4 illustrates a flow chart of the method steps according to the second aspect of the disclosure.
Figure 5:
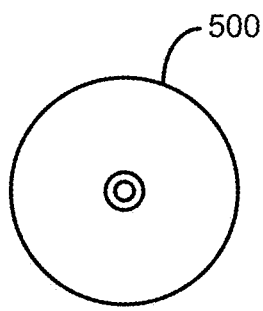
FIG. 5 illustrates a computer program product according to the third aspect of the disclosure.

FIG. 4 illustrates a flow chart of the method steps according to the second aspect of the disclosure.

The second aspect of this disclosure shows a method for determination of humidity of concrete. The method comprising the step of S1 obtaining first measurement data by a gauge A1,A2,A3 embedded into concrete, and the step of S6 transferring data wirelessly by a wireless communication module 10a, 10b, 10c for making a value, defining the humidity of the concrete, available at a remote location.

One advantage with this second aspect is that there is no need for a user to be in the vicinity of the concrete 1, instead the humidity of the concrete can be made available at a remote location and the transfer of data can occur on a continuous basis or when needed. There is further no need to drill a hole and wait for a humidity equilibrium since the gauge A1,A2,A3 is configured to be embedded into the concrete 1 from the beginning when the concrete object is built.

According to some embodiments the method further comprises the step of S2 determining the relative oxygen saturation % O at the gauge A1,A2,A3.

One advantage with this embodiment is that the gas at the gauge can be analyzed and a relative measure of the concentration of oxygen that is dissolved or carried in the concrete, as a proportion of the maximal concentration that can be dissolved in the concrete, can be determined.

According to some embodiments the method further comprises the step of S3 determining the humidity at the gauge A1,A2,A3 based on the determined relative oxygen saturation % O at the gauge A1,A2,A3.

One advantage with this embodiment is that the use of a humidity sensor can be eliminated and a determination of the humidity of the concrete at the gauge can instead be determined based on the determined relative oxygen saturation at the gauge.

According to some embodiments the method further the method comprises the step of S4 obtaining second measurement data by a reference gauge B1,B2,B3.

One advantage with this embodiment is that obtained second measurement data of the environment surrounding the concrete with the embedded gauge A1,A2,A3 can be used as reference data for determination of the humidity of the concrete at the gauge A1,A2,A3 embedded in the concrete.

According to some embodiments the method further the method comprises the step of S5 determining the humidity at the gauge A1,A2,A3 based on the first measurement data obtained by the gauge A1,A2,A3 and based on the second measurement data obtained by the reference gauge B1,B2, B3.

One advantage with this embodiment is that obtained first measurement data obtained by the gauge embedded in the concrete and obtained second measurement data of the environment surrounding the concrete with the embedded gauge, can be used for determination of the humidity of the concrete at the gauge embedded in the concrete.

The third aspect of this disclosure shows a computer program product the second aspect comprising a non-transitory computer readable medium, having thereon a computer program comprising program instructions, the computer program being loadable into a processing circuitry 102a, 102b, 102c and configured to cause execution of the method when the computer program is run by the at least one processing circuitry 102a, 102b,102c.

The person skilled in the art realizes that the present disclosure is not limited to the preferred embodiments described above. The person skilled in the art further realizes that modifications and variations are possible within the scope of the appended claims. Additionally, variations to the disclosed embodiments can be understood and effected by the skilled person in practicing the claimed disclosure, from a study of the drawings, the disclosure, and the appended claims.

The invention claimed is:

1. A system for determination of humidity of concrete, the system comprises:
 a gauge configured to be embedded into the concrete wherein the gauge comprises:
  an oxygen sensor, and
  an ammonia absorption system, wherein the ammonia absorption system is configured to absorb ammonia from the gas at the gauge for enhancing the accuracy of the gauge when obtaining measurement data;
 a first wireless communication module configured for wide area radio communication; and
 a processing circuitry operatively connected to the a gauge and the wireless communication module, configured to cause the system-to:
  obtain first measurement data by the gauge;
  determine the relative oxygen saturation at the gauge;
  determine the humidity at the gauge based on the determined relative oxygen saturation at the gauge; and
  transfer data wirelessly by the wireless communication module to a remote location.

2. The system according to claim 1, the system further comprises:
 a reference gauge configured to be placed in the environment surrounding the concrete with the embedded gauge,
 a second wireless communication module configured for wide area radio communication; and
 the processing circuitry is operatively connected to the reference gauge and configured to:
  obtain second measurement data by the reference gauge.

3. The system according to claim 2, wherein the processing circuitry is further configured to:
 determine the humidity at the gauge based on the first measurement data obtained by the gauge and based on the second measurement data obtained by the reference gauge.

4. The system according to claim 2, wherein the processing circuitry is further configured to:
 determine the humidity at the gauge based on the first measurement data obtained by the gauge and based on the second measurement data obtained by the reference gauge combined with chemical composition data of the concrete.

5. The system according to claim 1, wherein the gauge or the reference gauge further comprises a temperature sensor.

6. A method for determination of humidity of concrete, the method comprising:
- obtaining first measurement data by a gauge embedded into concrete, wherein the gauge comprises an oxygen sensor, and an ammonia absorption system, wherein the ammonia absorption system is configured to absorb ammonia from the gas at the gauge for enhancing the accuracy of the gauge when obtaining measurement data;
- determining the relative oxygen saturation at the gauge;
- determining the humidity at the gauge based on the determined relative oxygen saturation at the gauge; and
- transferring data wirelessly by a wireless communication module to a remote location.

7. The method according to claim 6, the method further comprising:
- obtaining second measurement data by a reference gauge placed in the environment surrounding the concrete with the embedded gauge.

8. The method according to claim 7, the method further comprising:
- determining the humidity at the gauge based on the first measurement data obtained by the gauge and based on the second measurement data obtained by the reference gauge.

9. A computer program product comprising a non-transitory computer readable medium, having thereon a computer program comprising program instructions, the computer program being loadable into processing circuitry and configured to cause execution of the method according to claim 6 when the computer program is run by the processing circuitry.

* * * * *